(12) United States Patent
Gillespie et al.

(10) Patent No.: US 6,764,452 B1
(45) Date of Patent: Jul. 20, 2004

(54) BONE GRAFT HARVESTER

(75) Inventors: Walter D. Gillespie, La Mesa, CA (US); David G. Matsuura, Escondido, CA (US); James F. Marino, La Jolla, CA (US); Corbett W. Stone, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/717,838

(22) Filed: Nov. 21, 2000

Related U.S. Application Data

(60) Provisional application No. 60/167,192, filed on Nov. 23, 1999.

(51) Int. Cl.[7] ............................................. A61B 10/00
(52) U.S. Cl. ................................... 600/567; 606/80
(58) Field of Search .................................. 600/562, 561, 600/567, 570; 606/79, 80, 81, 82, 83, 84, 85, 86, 179, 167, 169, 170, 171, 176, 177, 178, 180; 604/164.01–164.09; 433/165; 408/199; D15/138–139; D8/59

(56) References Cited

U.S. PATENT DOCUMENTS

| | | | |
|---|---|---|---|
| 4,646,738 A | 3/1987 | Trott | |
| 5,133,755 A | 7/1992 | Brekke | |
| 5,269,785 A | 12/1993 | Bonutti | |
| 5,322,505 A | 6/1994 | Krause et al. | |
| 5,411,514 A * | 5/1995 | Fucci et al. | 606/180 |
| 5,632,747 A | 5/1997 | Scarborough et al. | |
| 5,741,261 A | 4/1998 | Moskovitz et al. | |
| 5,833,692 A * | 11/1998 | Cesarini et al. | 606/79 |
| 5,851,208 A | 12/1998 | Trott | |
| 5,876,405 A * | 3/1999 | Del Rio et al. | 606/80 |
| 6,030,364 A * | 2/2000 | Durgin et al. | 604/164 |
| 6,179,615 B1 * | 1/2001 | Blacklock et al. | 433/165 |

FOREIGN PATENT DOCUMENTS

| | | |
|---|---|---|
| WO | WO 98/25539 | 6/1998 |
| WO | WO 00/45712 | 8/2000 |
| WO | WO 00/45713 | 8/2000 |

* cited by examiner

*Primary Examiner*—Max F. Hindenburg
*Assistant Examiner*—Pamela L. Wingood
(74) *Attorney, Agent, or Firm*—Jonathan Spangler

(57) ABSTRACT

A bone graft harvesting drill, comprising: a flexible tubular member and a hollow cylindrical drill bit mounted to a distal end of the flexible tubular member.

14 Claims, 20 Drawing Sheets

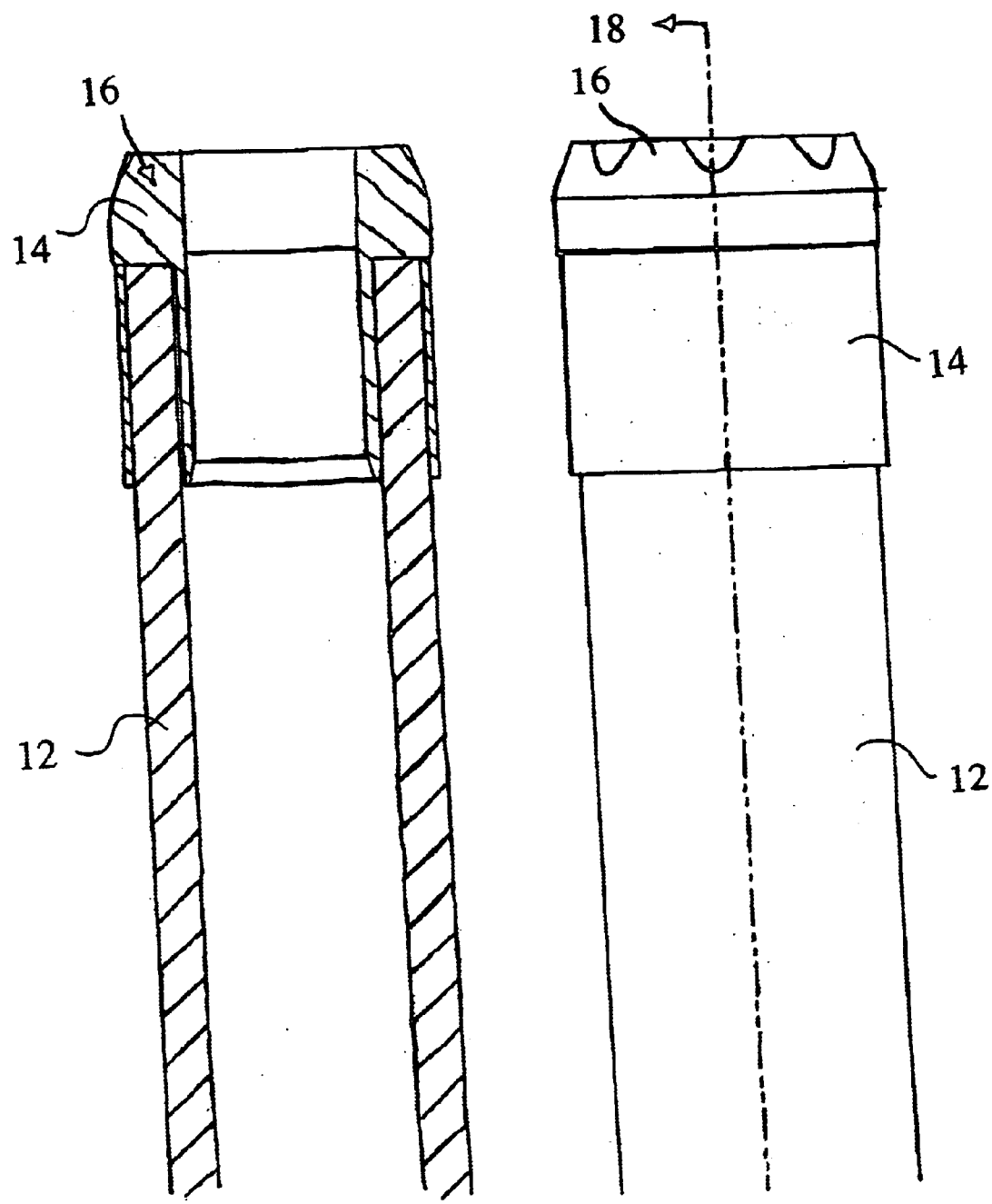

SECTION A-A

BONE GRAFT HARVESTER

CROSS-REFERENCES TO RELATED APPLICATIONS

This application claims the benefit of prior provisional application no. 60/167,192 filed Nov. 23, 1999, the full disclosure of which is incorporated herein by reference.

The present invention relates to systems for removing bone graft material from a patient, and in particular to systems for removing bone graft material from a patient's ilium.

SUMMARY OF THE INVENTION

The present invention provides a bone graft harvesting drill comprised of a flexible tubular member having a hollow cylindrical drill bit mounted at its distal end. An advantage of the present harvesting drill is that it can be used to remove softer cancellous bone from between the harder cortical plates of the patient's ilium. Specifically, the present harvesting drill can be advanced in a path between the plates of the ilium, with the drill automatically tending to deflect off the hard cortical surfaces of the bone such that the drill instead bores a path therebetween through the cancellous bone material.

In preferred aspects, the drill bit has a plurality of wavy or sinusoidal teeth which may be sharpened such that the outer surfaces of the teeth taper inwardly towards their distal ends, wherein the inner surfaces of the teeth are aligned with the walls of the drill bit. An advantage of sharpening the teeth such that their outer surfaces slant inwardly while their inner surfaces remain parallel is that as the outer surface of the distal tip of the drill bit comes into contact with the curved inner surface of the cortical plate of the patient's ilium, the bevel or chamfer at the distal tip causes the distal tip to deflect away from the cortical bone. As the main body of the drill is flexible in radial directions, (i.e.: perpendicular to a longitudinally extending axis passing therethrough), and is preferably relatively rigid in compression along the longitudinal axis of the drill, a transverse load on the beveled end of the drill bit results in a "passive steering" condition. This "passive steering" feature of the device allows the harvesting drill to take the desired path of least resistance through the softer cancellous bone while preserving the harder cortical bone. Should the outermost edges of the drill tip instead be sharp, and not beveled or chamfered, the drill bit may instead have a tendency to catch the inner surface of the cortical bone and would undesirable pass through the ilium into the surrounding tissue. Another advantage of the beveled tip is that it is easier to push the drill through the bone during cutting.

In preferred aspects, an optional tissue removing insert is slidably received through the inner bores of the flexible tubular member and the drill bit. This tissue removing insert is specifically adapted to anchor into and, when rotated, tear away tissues which have become disposed within the inner bore of the drill bit.

In further optional aspects of the present invention, inwardly facing projections are found on the drill bit. These projections are specifically adapted to tear away tissues which have become disposed within the inner bore of the drill bit. In preferred aspects, the inwardly facing projection is formed from a C-shaped or L-shaped cut through the wall of the drill bit wherein the inner flange is bent inwardly into the bore of the drill bit. In alternate preferred aspects, a blade spans across the bore of the drill bit to tear away tissues protruding therein. An advantage of this embodiment of the invention is that the blade acts as a morcillator to premasticate the tissue prior to placement into the patient.

In a preferred method of using the present invention, the flexible tube and attached drill bit are rotated, however, they may instead be oscillated such that they preferentially cut through the softer cancellous tissues, avoiding harder cortical tissues.

BRIEF DESCRIPTION OF THE DRAWINGS

FIG. 17 is a side elevation view of the distal tip of the present invention.

FIG. 18 is a sectional view corresponding to line 18 in FIG. 17.

DESCRIPTION OF THE SPECIFIC EMBODIMENTS

Figure 1:
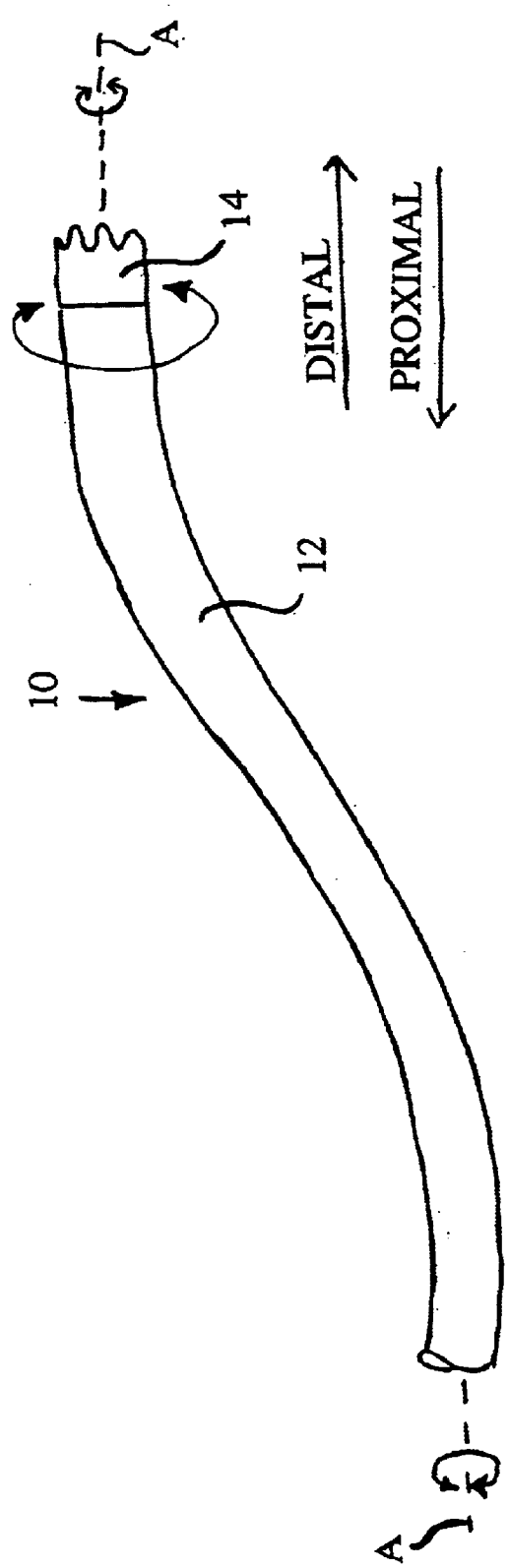
FIG. 1 is a perspective view of the present invention.

Referring to FIG. 1, the present invention comprises a bone graft harvesting drill 10 comprised of a flexible tubular member 12 with a hollow cylindrical drill bit 14 mounted to the distal end of the flexible tubular member 12 as shown. Preferably, the tubular member 12 is made from a biocompatable thermoplastic such as polyethylene or polypropylene, however, many other plastics could be used.

The drill bit 14 is preferably made from stainless steel, however, other materials could be used, such as hard metals or hard thermoplastics.

Figure 2:
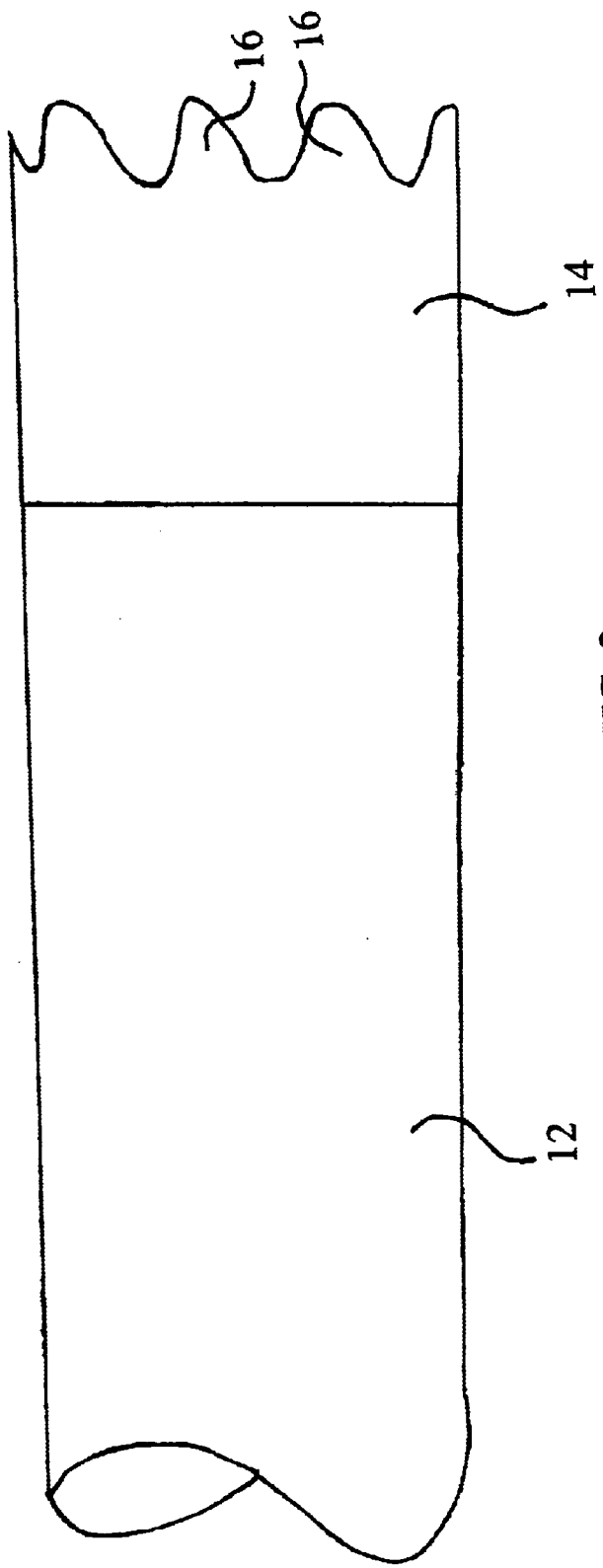
FIG. 2 is a close-up of the distal end of the present invention.

As can be seen in FIG. 2, drill bit 14 has a plurality of teeth 16 which wrap around its circumference. Preferably, teeth 16 are "wavy" or sinusoidal in shape as shown. An advantage of such a serrated tooth is that it is non-clogging, as opposed to a typical triangular saw tooth, which has a tendency to catch materials in the spaces between the teeth. A further advantage is that the aggressiveness of the tip of the drill is more easily controlled in the serrated type tip than in more conventional saw tooth forms. If the bit becomes too aggressive, damage to the inner planes of the cortical bone may occur. Furthermore, the serrated type tip is much easier and more cost effective to manufacture than conventional saw tooth forms.

Figure 3:
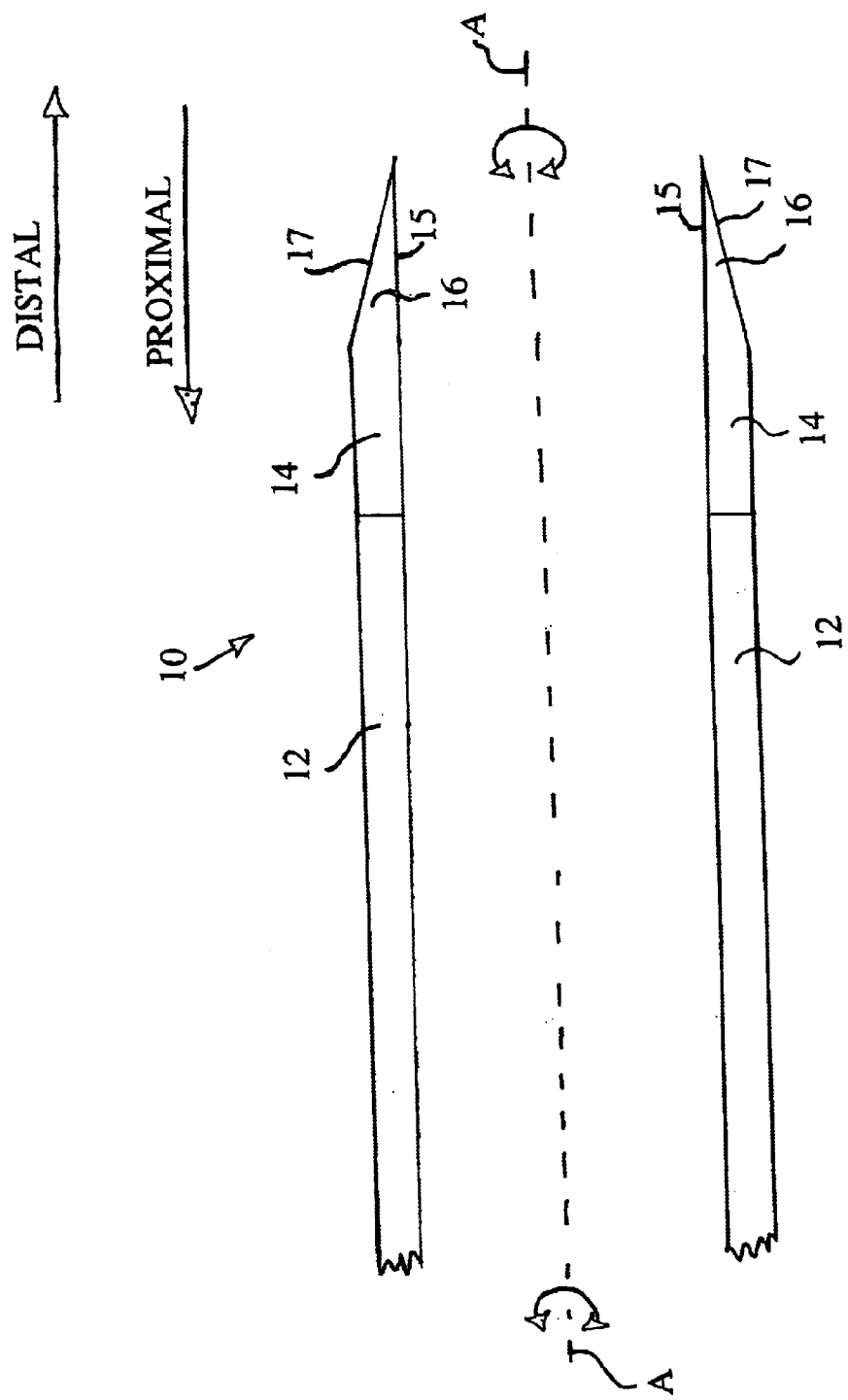
FIG. 3 is a sectional view of the distal end of the present invention.

Referring to FIG. 3, a sectional view of drill 10 is shown. Teeth 16 have inner surfaces 15 and outer surfaces 17. In a preferred aspect, outer surfaces 17 taper inwardly towards the distal end of drill 10. Inner surfaces 15 are preferably aligned parallel with one another and parallel with the outer surface of drill bit 14 as shown. An advantage of having outer surfaces 17 taper inwardly (as opposed to having inner surfaces 15 tapered outwardly), is that the drill bit 14 can be advanced to cut into tissues more easily.

Figure 4:
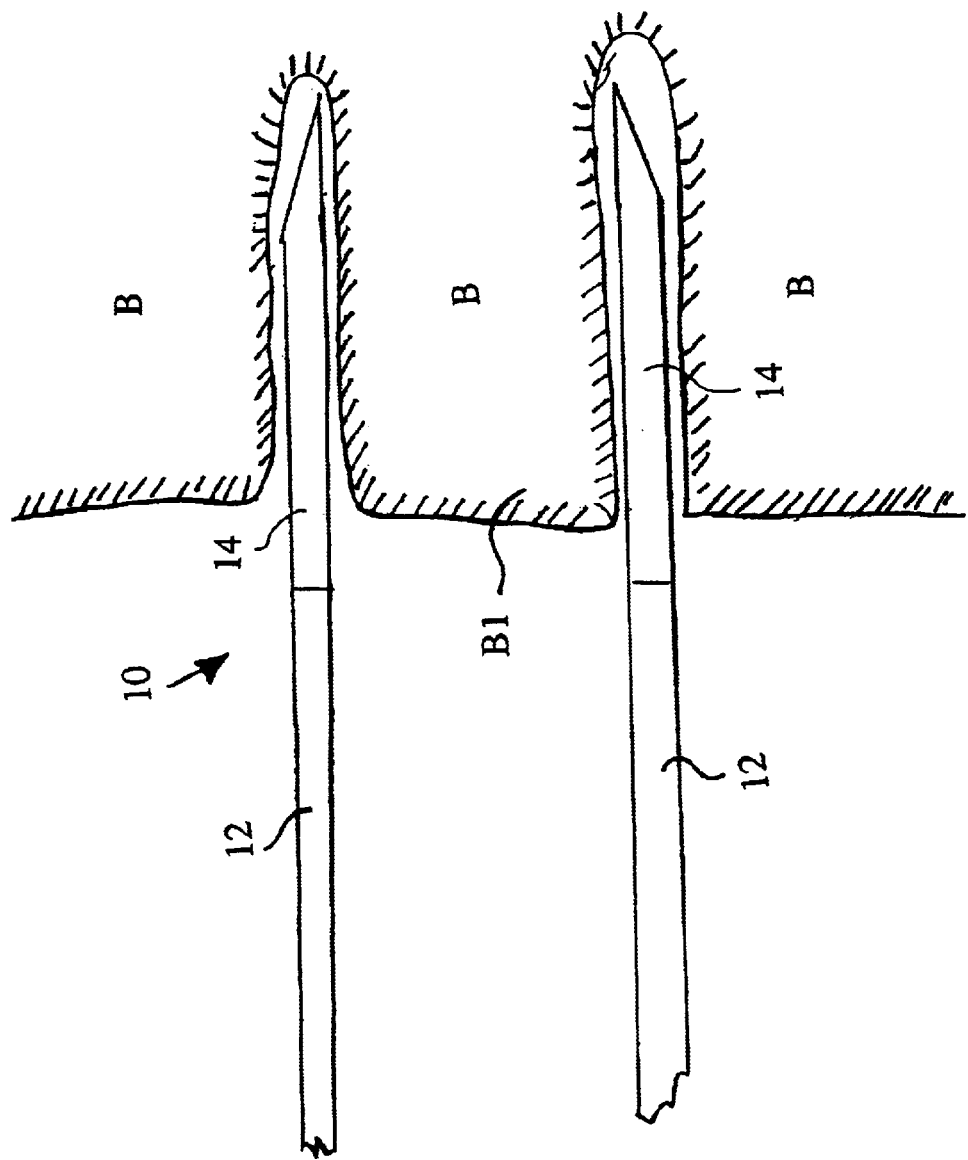
FIG. 4 is a sectional view of the distal end of the present invention showing in the present invention cutting into a bone.

FIG. 4 shows drill 10 cutting into bone B. In a preferred aspect of the invention, drill 10 is rotated, about a central longitudinal axis A extending therethrough.

Figure 5:
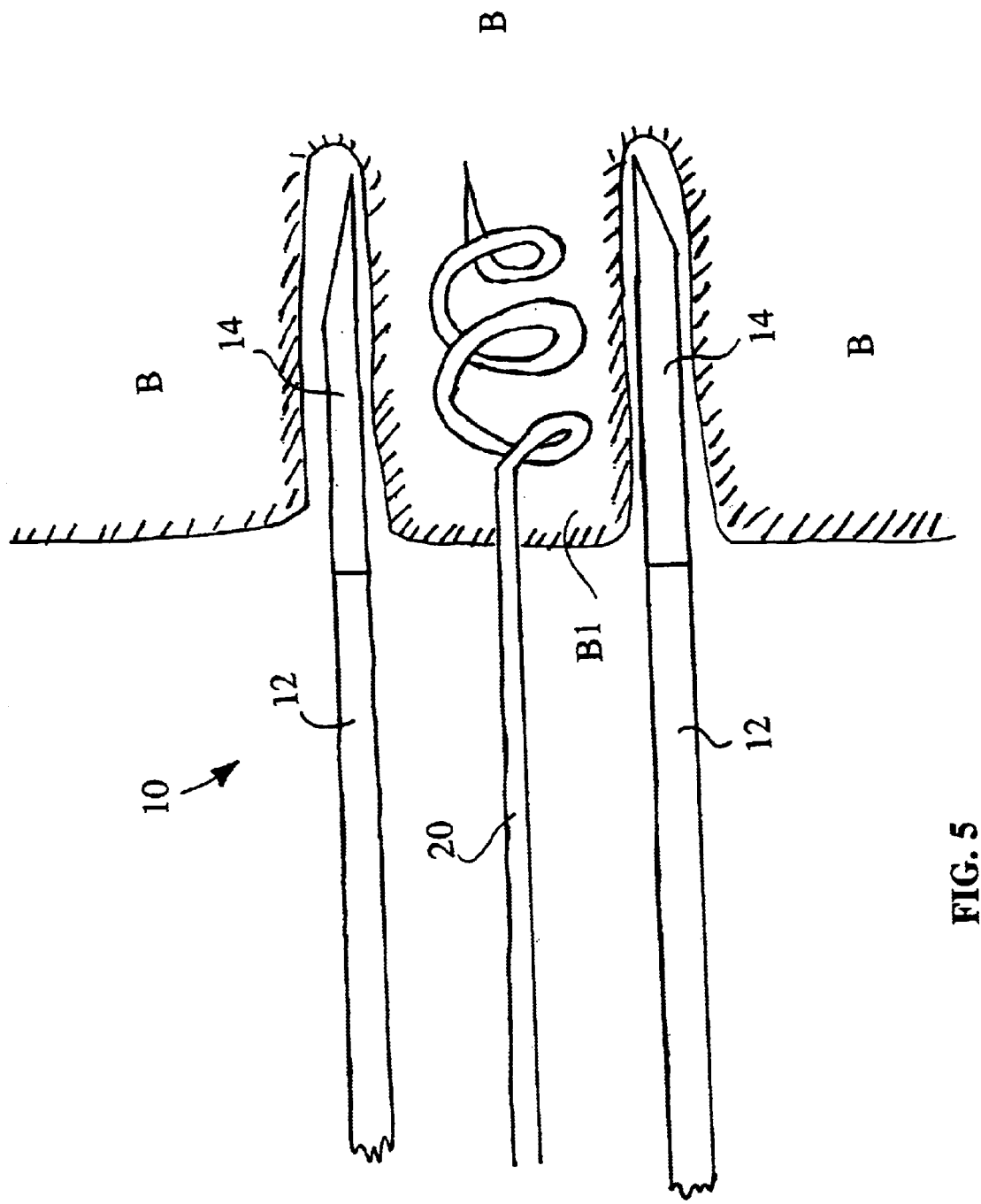
FIG. 5 corresponds to FIG. 4, but shows a tissue removing insert anchored into a tissue mass protruding into the inner bore of the present invention.
Figure 6:
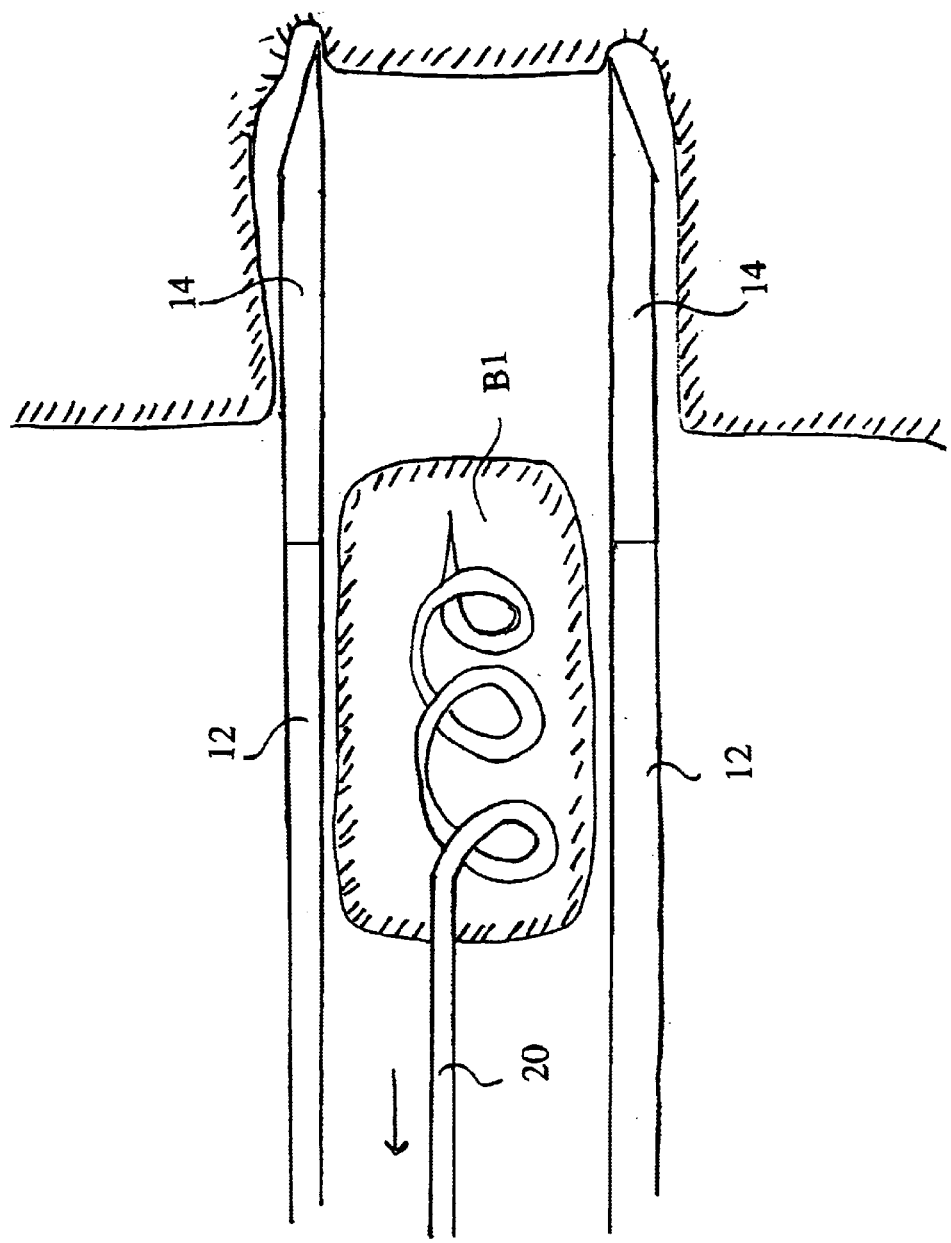
FIG. 6 shows removal of the tissue mass from the inner bore of the invention.

As seen in FIG. 4, a mass of bone tissue B1 will enter into the central bore of drill 10 as drill 10 is cut into the bone. In an optional preferred aspect of the present invention, a tissue removing insert 20 is introduced into the central bore of drill 10 as shown in FIG. 5. Insert 20 may comprise a screw-type mechanism as illustrated, or any other system for gripping into and tearing away tissue mass B1. As seen in FIG. 6, insert 20 is used to tear away and remove tissue mass B1 from the inner bore of drill 10, such that tissue mass B1 can be used as bone graft material. The sequence of steps illustrated in FIGS. 4, 5, and 6 can preferably be repeated again and again as drill 10 advances further and further into bone B.

Figure 7:
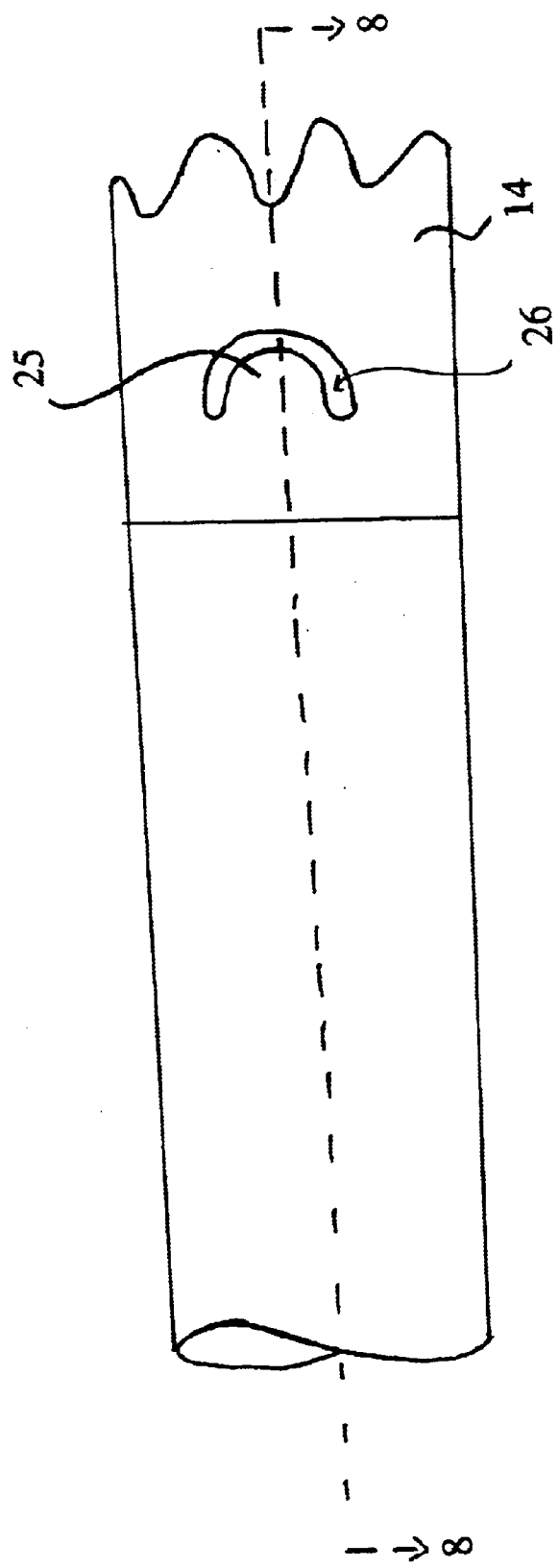
FIG. 7 is a side elevation view of an embodiment of the invention having an inwardly facing projection in the drill bit.
Figure 8:
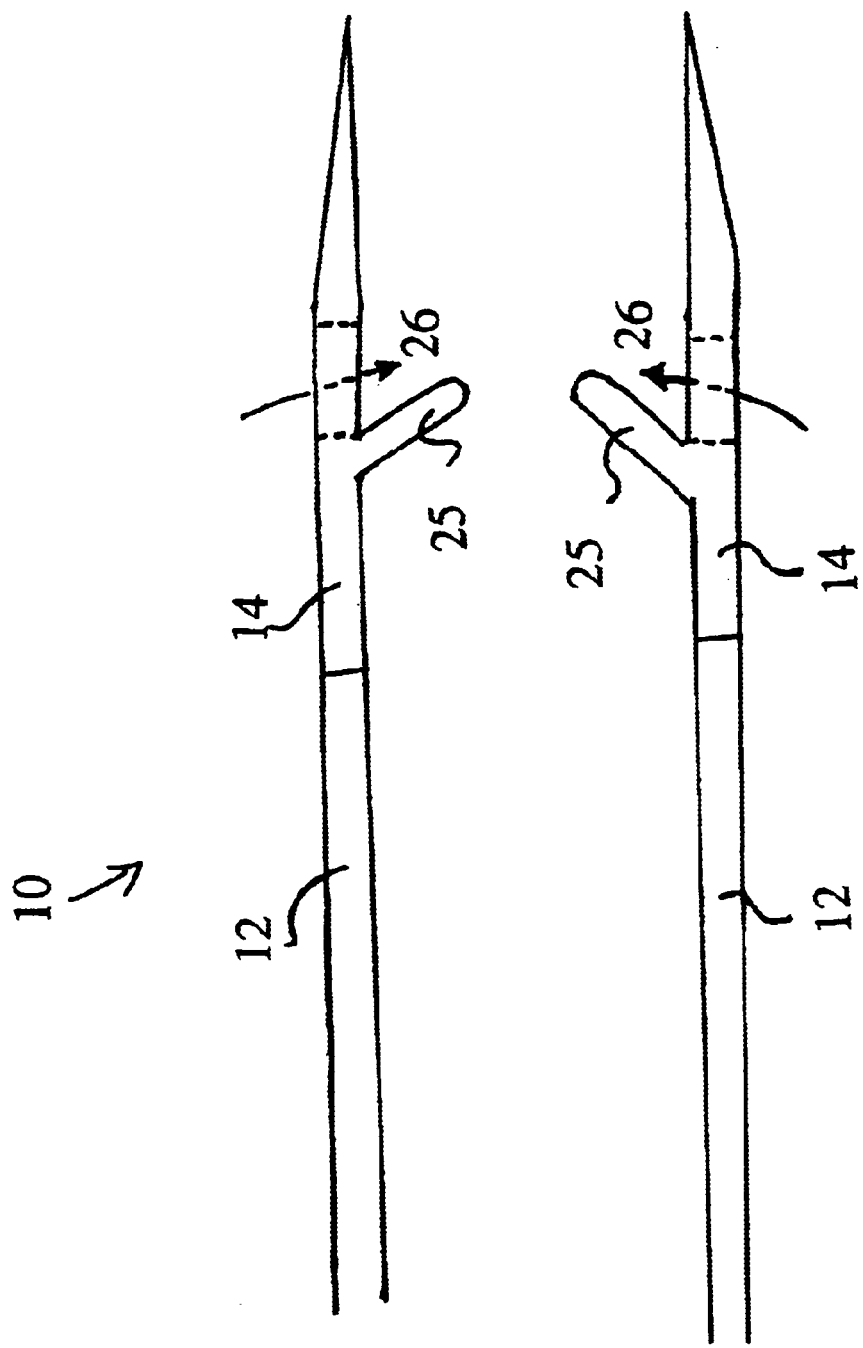
FIG. 8 is a view corresponding to line 8—8 in FIG. 7.

An additional preferred aspect of the invention is illustrated in FIGS. 7 and 8 in which an inwardly facing projection 25 which may be formed by a C-shaped cut 26 in drill bit 14 is found. Specifically, as seen in FIG. 8, projection 25 is bent to face inwardly into the inner bore of drill 10. An advantage of the projections 25 facing inwardly are that as drill 10 is advanced, projections 25 will tend to tear away tissue protruding therein such that the tissue can easily be removed from the central bore of drill such that it can be used for bone graft purposes. In preferred aspects, a plurality of projections 25 can be disposed around the circumference of drill bit 14. Preferably, such inwardly facing projections 25 will be disposed equidistantly around the circumference of drill bit 14. In preferred aspects, two, three, four or more of inwardly facing projections 25 may be used.

Figure 9:
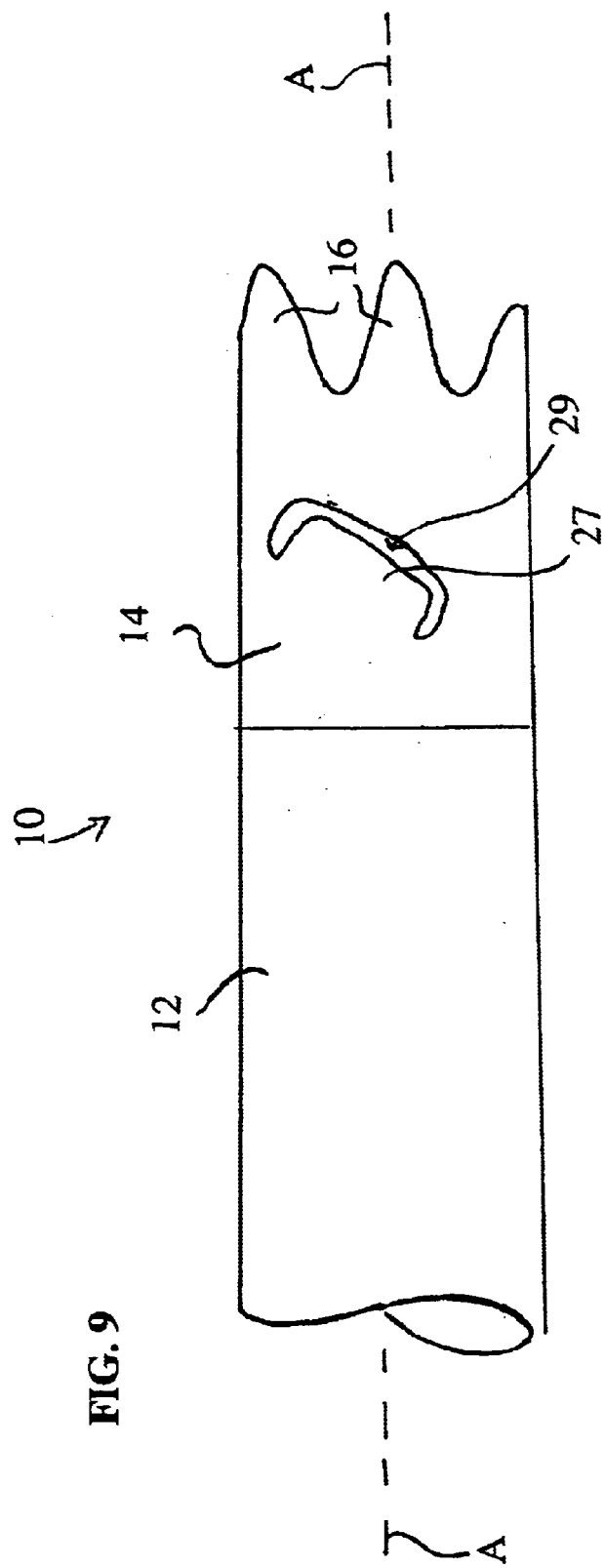
FIG. 9 is similar to FIG. 7, but shows the inwardly facing projection posed at an angle.

FIG. 9 shows an inwardly facing projection 27 formed by a C-shaped cut 29 wherein projection 27 is disposed at an angle to axis A. An advantage of projection 27 being angled to axis A is that it will tend to screw into the tissue mass disposed within the inner bore of drill 10, such that the tissue mass can be more easily torn away and removed.

Figure 10:
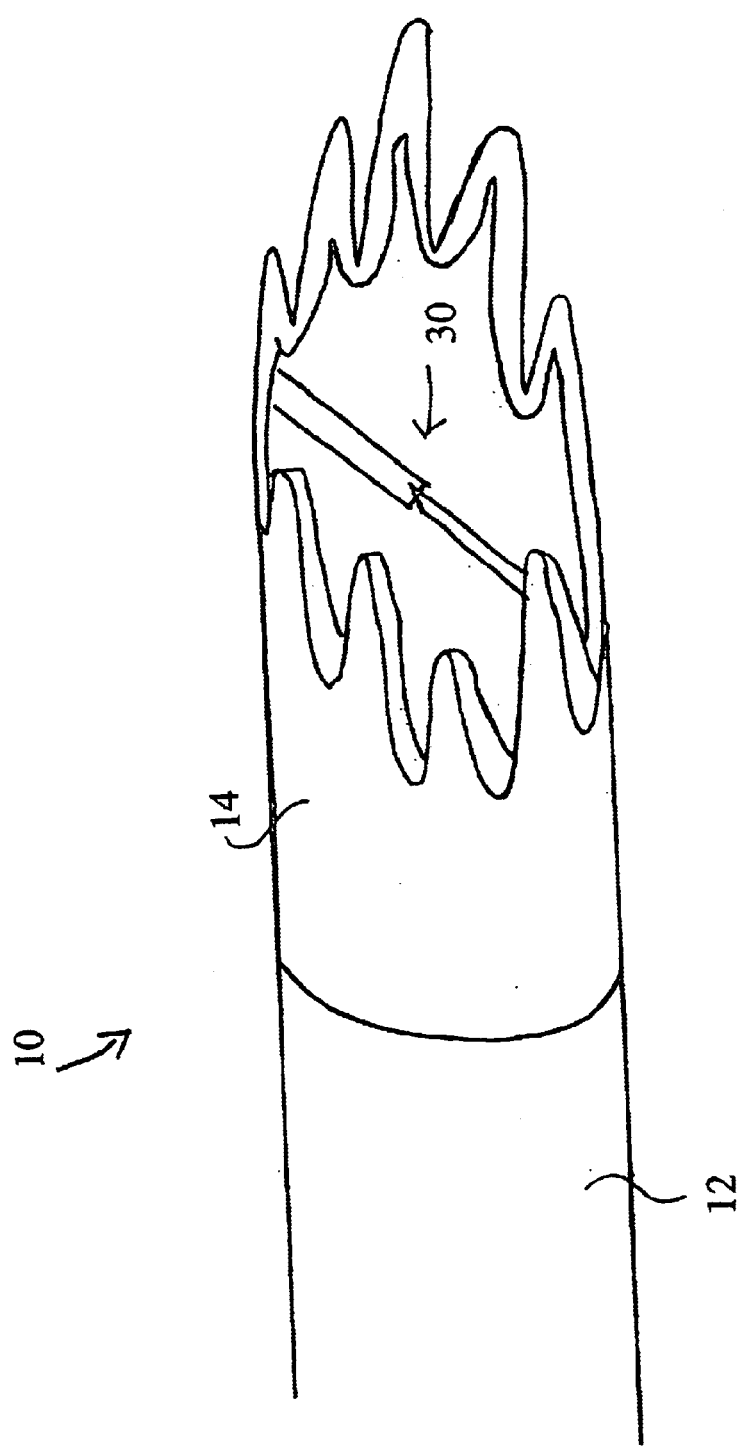
FIG. 10 shows an embodiment of the distal end of the present invention using a blade spanning across the inner bore of the drill bit.
Figure 11:
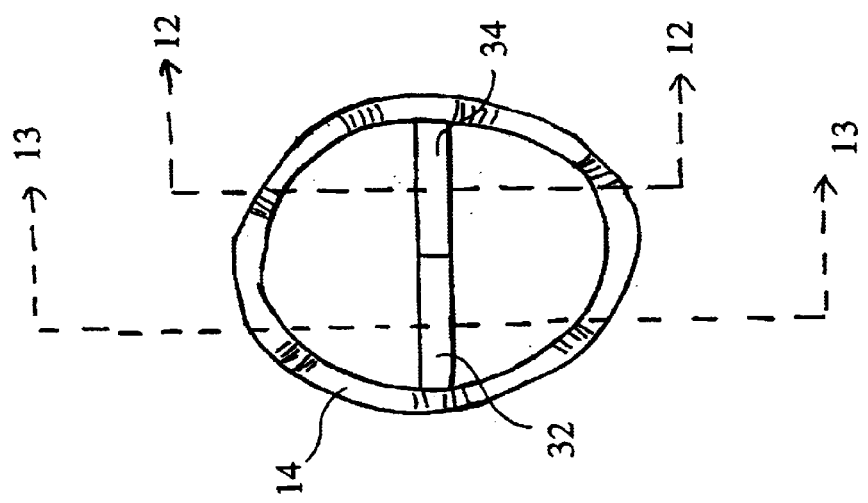
FIG. 11 is a front view corresponding to FIG. 10.
Figure 12:
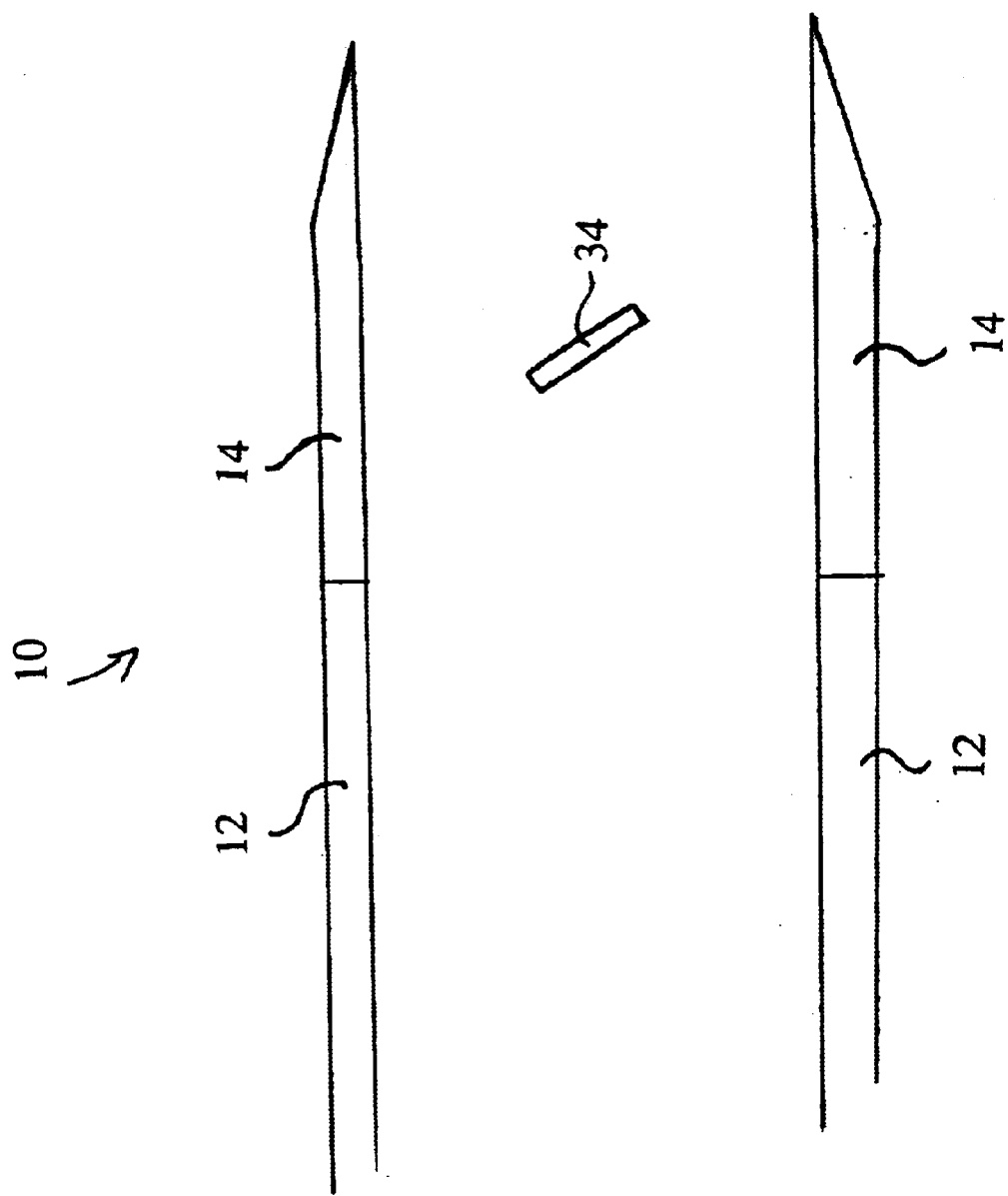
FIG. 12 is a view taken along line 12—12 in FIG. 11.
Figure 13:
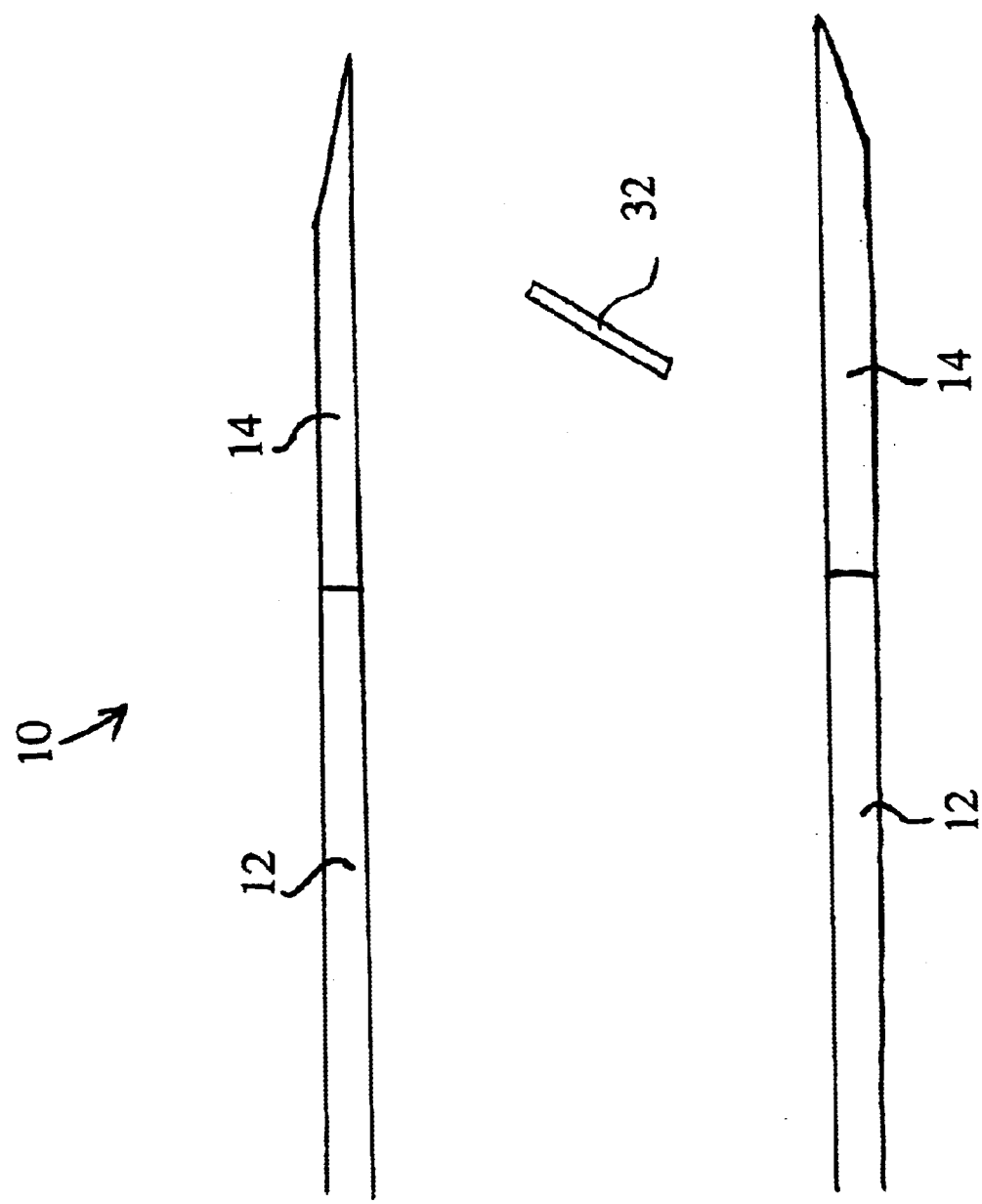
FIG. 13 is a view taken along line 13—13 in FIG. 11.
Figure 14:
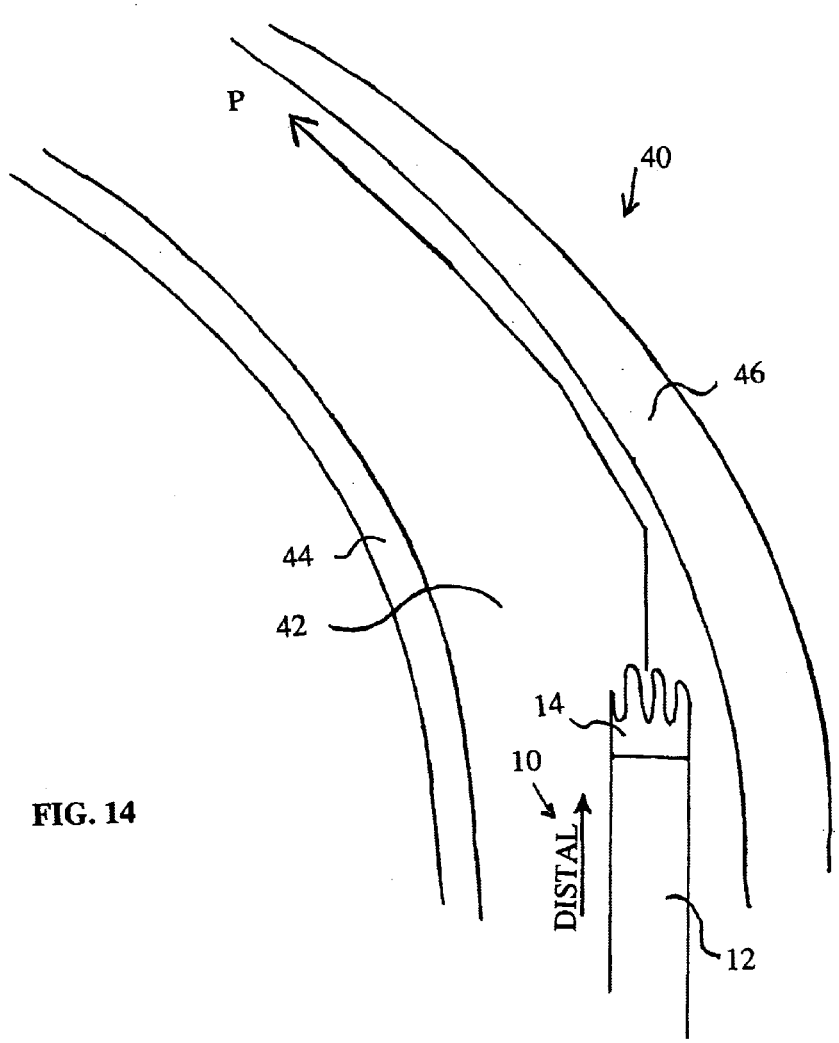
FIG. 14 is an illustration of the direction of travel of the present invention it moves between the tables of the ilium.
Figure 15:
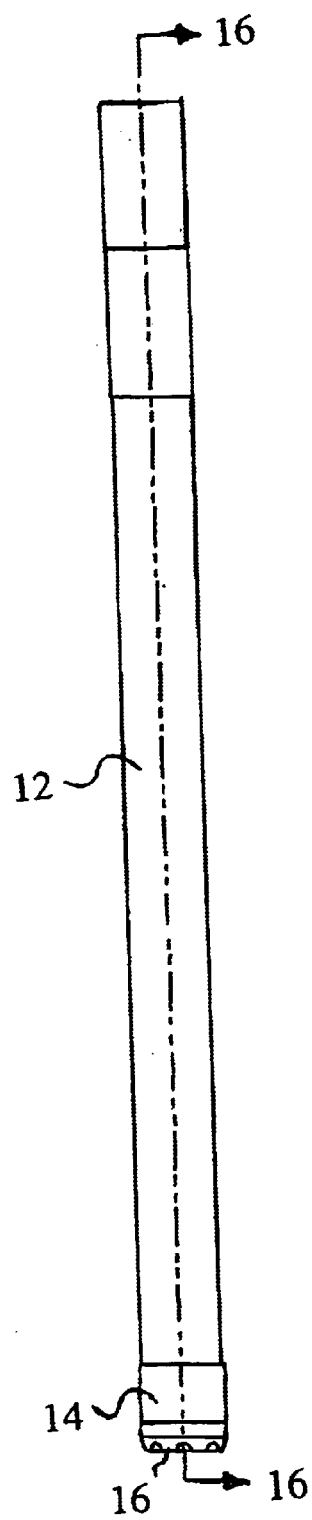
FIG. 15 is a side elevation view of the present invention.
Figure 16:
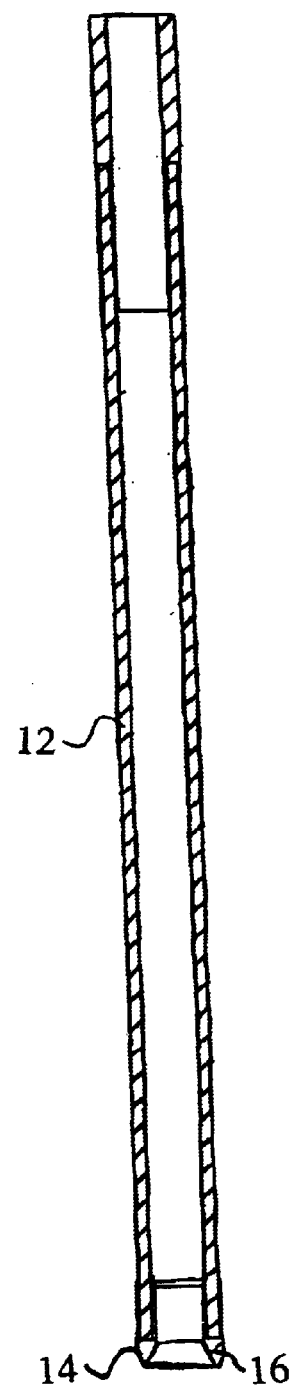
FIG. 16 is a sectional view corresponding to line 16—16 in FIG. 15.

FIG. 10 shows an alternate embodiment of the present invention in which a blade 30 spans across the bore of drill bit 14 as shown. As can be seen more clearly in FIGS. 11, 12, and 13, blade 30 may comprise two sections 32 and 34 which may be oppositely angled such that as drill 10 is rotated, each of blades 32 and 34 cut into the tissue which becomes disposed within the inner bore of drill bit 14 such that the tissue can be easily removed from the inner bore of drill bit 14.

FIGS. 14 and 22 to 24 show a preferred direction of travel for drill 10 wherein drill 10 is introduced into ilium 40 into a region of cancellous bone 42 disposed between ilium tables 44 and 46. Tables 44 and 46 comprise a very hard cortical bone. As such, as drill 10 is advanced in a distal direction, drill bit 14 will tend to be deflected along table 46 such that it cuts through cancellous bone 42, without cutting through either 15 of tables 44 or 46. This is achieved by tube 12 being flexible such that it is able to respond to deflections of movement of drill bit 14 as drill 10 travels along path P as shown.

Figure 21:
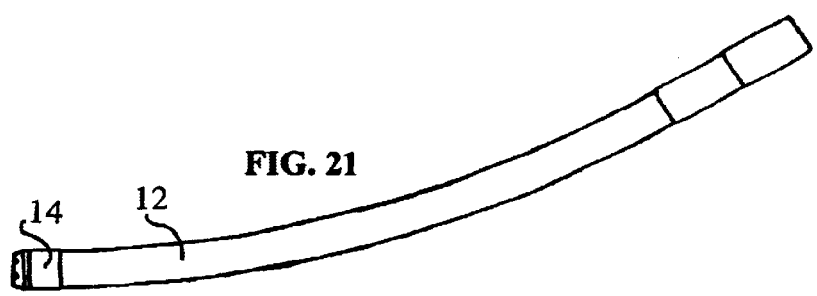
FIG. 21 is a side elevation view corresponding to FIGS. 19 and 20.
Figure 20:
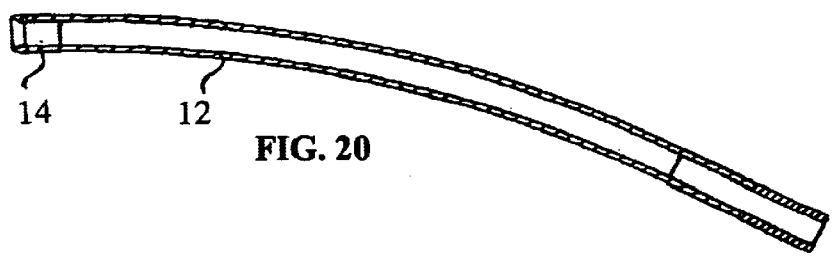
FIG. 20 is a sectional view corresponding to line 20—20 in FIG. 19.
Figure 19:
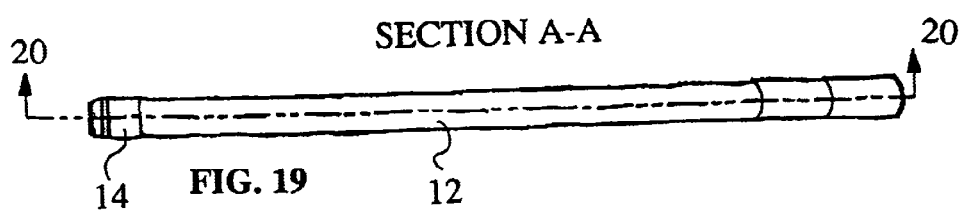
FIG. 19 is a side elevation view of the present invention.
Figure 22:
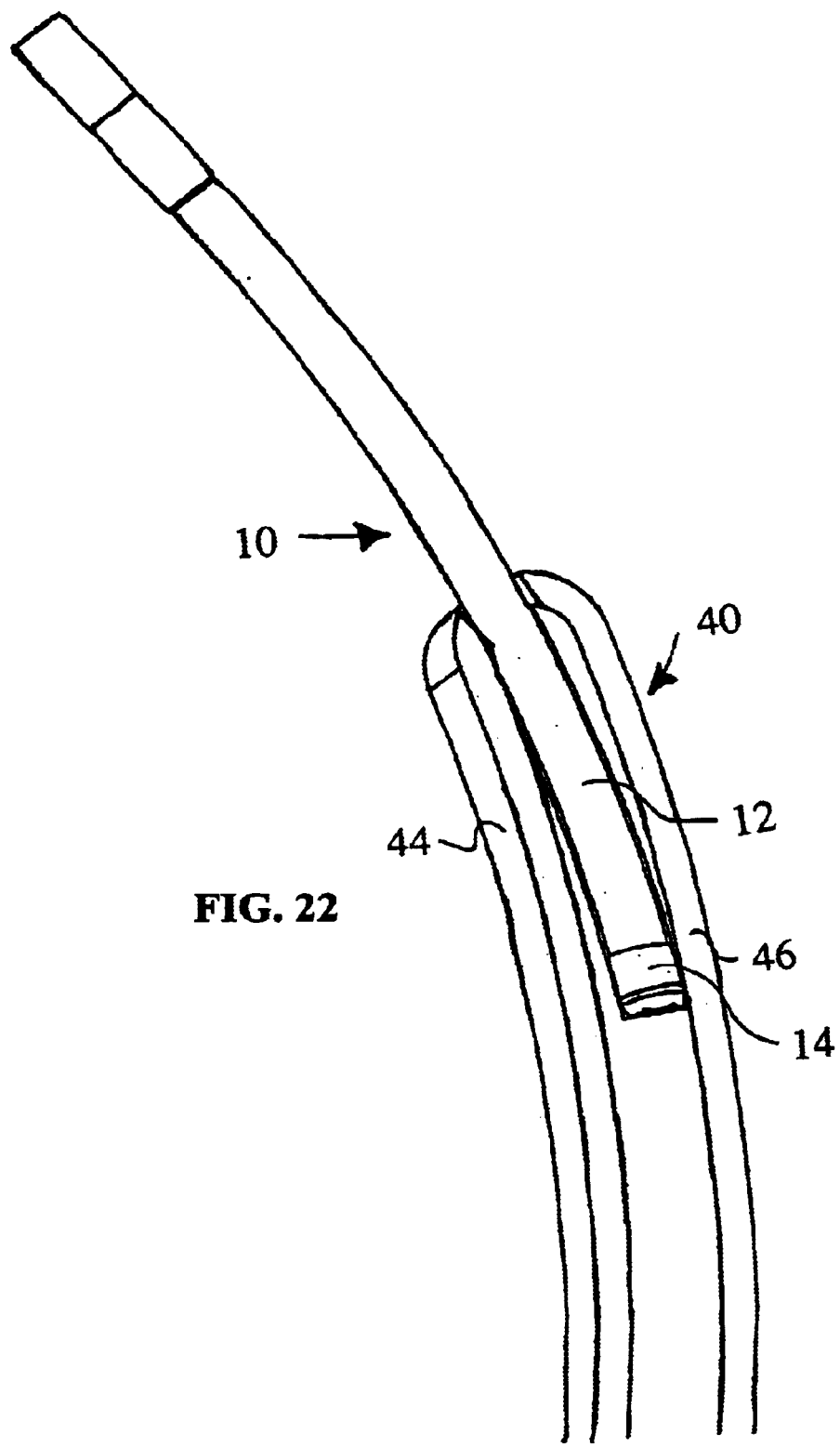
FIG. 22 is a schematic view of the present drill positioned between the tables of the ilium.
Figure 23:
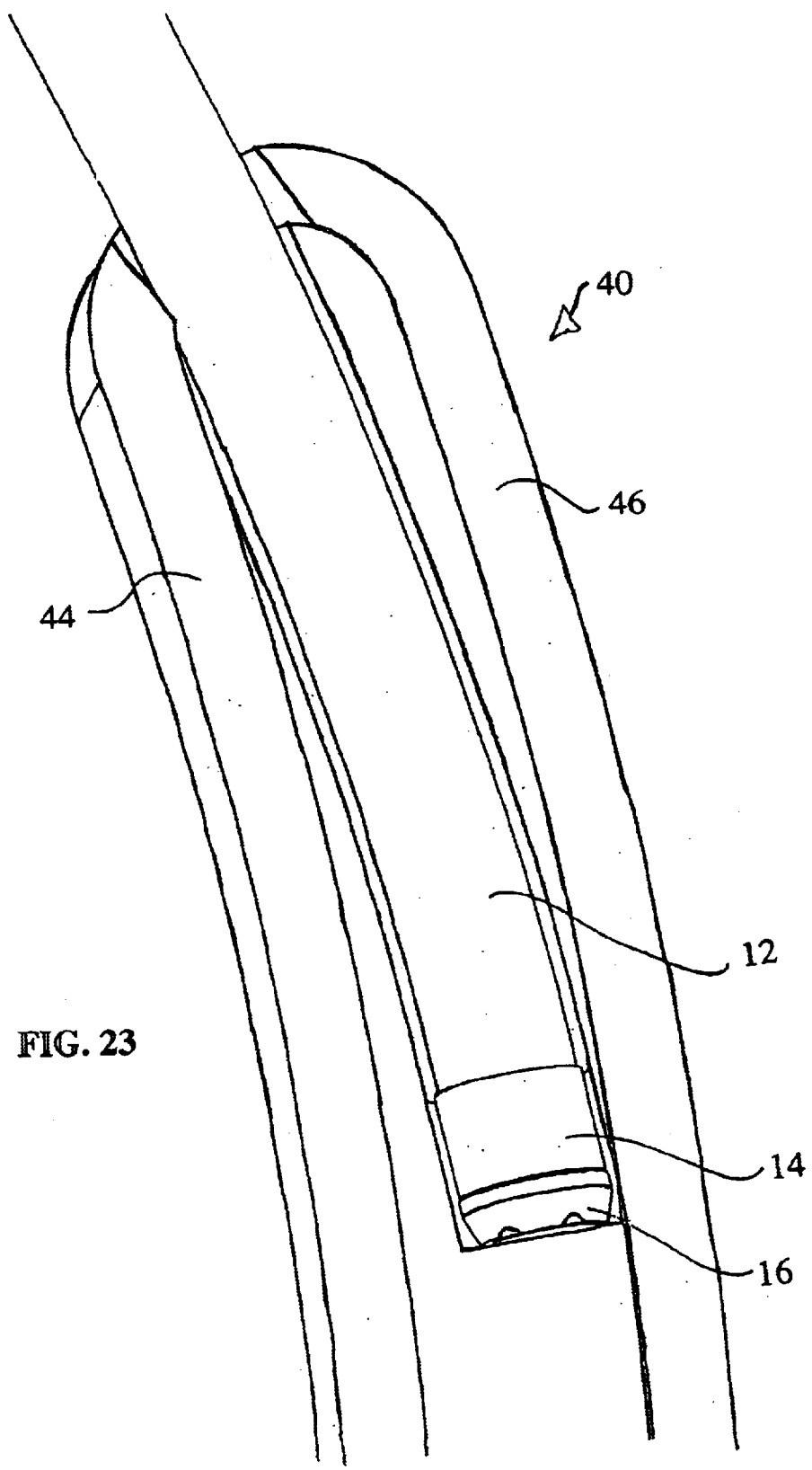
FIG. 23 is a close-up view of corresponding to FIG. 22.
Figure 24:
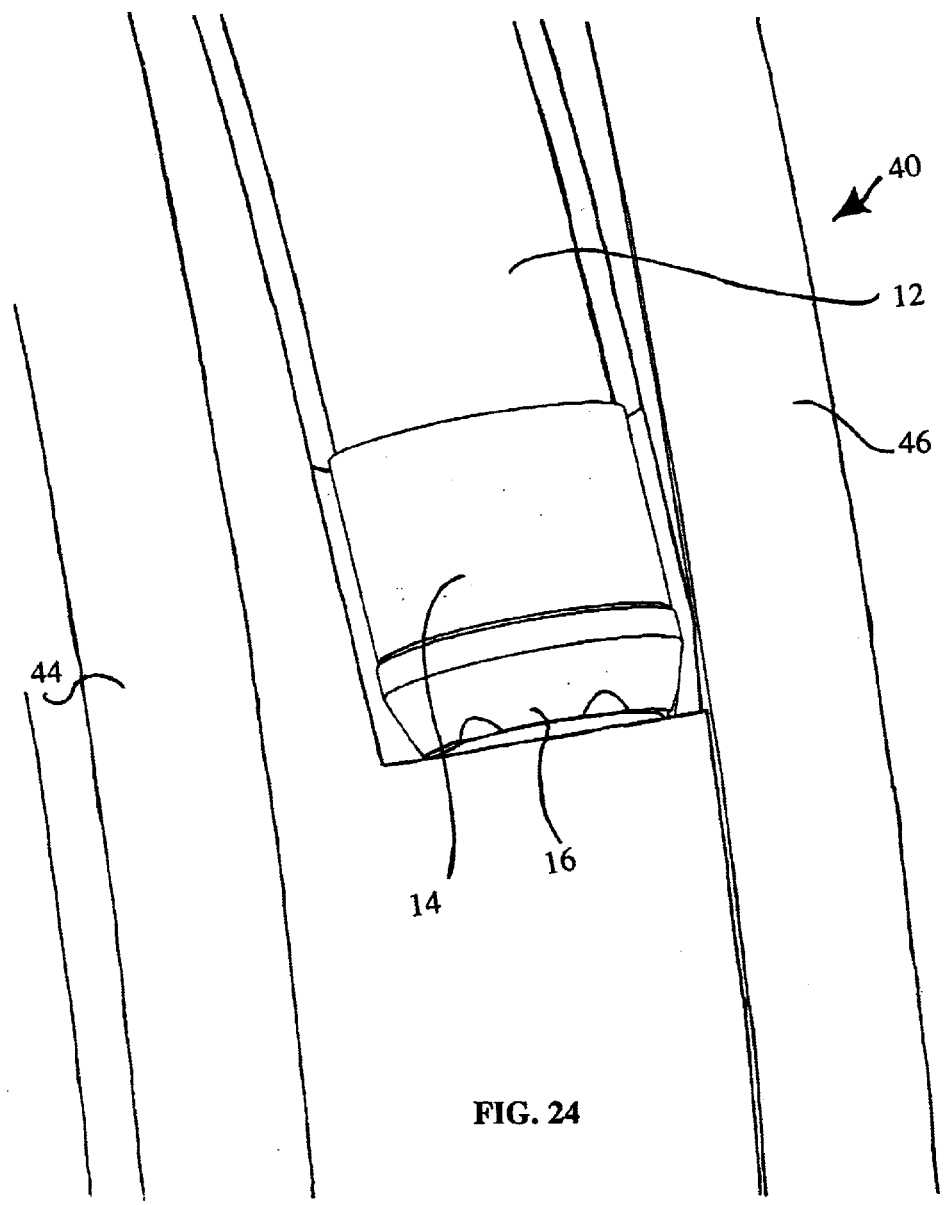
FIG. 24 is a close-up view of corresponding to FIG. 23.

Bending of flexible tubular member 12 is also shown in FIGS. 20 and 21.

What is claimed is:

1. A bone graft harvesting drill, comprising:
    a flexible tubular member; and
    a cylindrical drill bit mounted to a distal end of the flexible tubular member,
    wherein the drill bit has a plurality of teeth having outer surfaces tapering inwardly towards their distal ends.

2. The bone graft harvesting drill of claim 1, wherein said cylindrical drill bit includes a hollow inner bore, and further comprising:
    a tissue removing insert received within the hollow inner bore of the drill bit.

3. The bone graft harvesting drill of claim 2, wherein the tissue removing insert is adapted to be slidably positioned within the inner bore of the drill bit.

4. The bone graft harvesting drill of claim 1, wherein the drill bit comprises an inner bore, and at least one projection facing inwardly into the inner bore of the drill bit and dimensioned to tear away tissues disposed within the inner bore of the drill bit.

5. The bone graft harvesting drill of claim 4, wherein the at least one projection comprises a plurality of inwardly facing projections disposed equidistantly around the circumference of the drill bit.

6. The bone graft harvesting drill of claim 4, wherein the at least one projection is formed from a C-shaped or L-shaped cut passing through the wall of the drill bit.

7. The bone graft harvesting drill of claim 4, wherein the at least one projection comprises a blade spanning across the inner bore of the drill bit.

8. A method of harvesting bone graft material, comprising:
    inserting a distal end of a hollow cylindrical drill into a patient's ilium, the distal end of a hollow cylindrical drill comprising a flexible tubular member, with a hollow cylindrical drill bit mounted to the distal end of the flexible tubular member; and
    rotating or oscillating the flexible tubular member about a longitudinal axis extending therethrough; and,
    advancing the hollow cylindrical drill such that cut away tissue is deposited in the inner bore of the hollow cylindrical drill.

9. The method of claim 8, wherein the hollow cylindrical drill is advanced such that the distal end of the cylindrical drill bit deflects off an inner boundary of the outer surface of the ilium, thereby cutting the cancellous bone while avoiding cutting cortical bone.

10. The method of claim 8, further comprising:

slidably inserting a tissue removal insert into the inner bores of the flexible tubular member and cylindrical drill bit;

anchoring the tissue removal insert into a mass of tissue protruding into the bore of the cylindrical drill bit;

tearing away the mass of tissue by rotating the tissue removal insert; and removing the mass of tissue from within the bore of the cylindrical drill bit by slidably removing the tissue removal insert from the inner bore of the cylindrical drill bit.

11. The method of claim 8, further comprising:

tearing away a mass of tissue protruding into the bore of the cylindrical drill bit with a protrusion which faces inwardly from an inner wall of the cylindrical drill bit into the bore of the cylindrical drill bit.

12. The method of claim 8, further comprising:

tearing away a mass of tissue protruding into the bore of the cylindrical drill bit with a blade spanning across the bore of the drill bit.

13. The method of claim 8, wherein the hollow cylindrical drill is inserted in a percutaneous cannulated approach.

14. A method of drilling bone, comprising:

providing a generally cylindrical drill bit having a beveled outer distal periphery;

inserting said generally cylindrical drill bit through an aperture formed in a patient's cortical bone; and rotating said generally cylindrical drill bit such that, when advanced through said aperture, said drill bit deflects off an inner wall of said cortical bone and thereby avoids penetrating said cortical bone other than through said aperture.

* * * * *